United States Patent [19]
Kaneda et al.

[11] 4,037,587
[45] July 26, 1977

[54] VALVE ASSEMBLY FOR A SPHYGMOMANOMETER

[75] Inventors: Nobuo Kaneda, Komae; Takenosuke Tokisono, Tokyo; Teizo Uchida, Kawaguchi, all of Japan

[73] Assignee: Bristoline Inc., Island Park, N.Y.

[21] Appl. No.: 665,703

[22] Filed: Mar. 11, 1976

[51] Int. Cl.² .............................................. A61B 5/02
[52] U.S. Cl. .............................. 128/2.05 G; 128/274; 137/625.28; 137/625.38; 251/330
[58] Field of Search ..................... 128/2.05 G, 2.05 M, 128/2.05 R, 2.05 C, 274; 137/625.28, 625.38; 251/330

[56] References Cited
U.S. PATENT DOCUMENTS

| | | | |
|---|---|---|---|
| 2,603,210 | 7/1952 | Puig | 128/2.05 G |
| 3,254,671 | 6/1966 | Berliner | 128/2.05 G X |
| 3,779,236 | 12/1973 | Stewart | 128/2.05 G |
| 3,823,707 | 7/1974 | Hayes | 128/2.05 G |

FOREIGN PATENT DOCUMENTS 2,118,295  10/1972  Germany ..................... 128/2.05 G

*Primary Examiner*—Kyle L. Howell
*Attorney, Agent, or Firm*—Kirschstein, Kirschstein, Ottinger & Frank

[57] ABSTRACT

An improved air bleed or full air discharge control valve assembly for a sphygmomanometer cuff in which a stem of the valve extends through and, in idle condition of the valve, sealingly engages the central opening of a resilient O-ring and is manipulated to release air either by being manually tilted about its inner end against a restoring force to temporarily enlarge the opening and thus provide a transient gap between the opening and the valve stem for accurately controlled bleed of air from the cuff during blood pressure measurements as long as the stem is tilted, or by being shifted axially to assume and maintain a position in which it permits rapid total air egress from the cuff through a central axial bore in the stem and at least one transverse opening from the bore to the outer surface of the stem.

8 Claims, 6 Drawing Figures

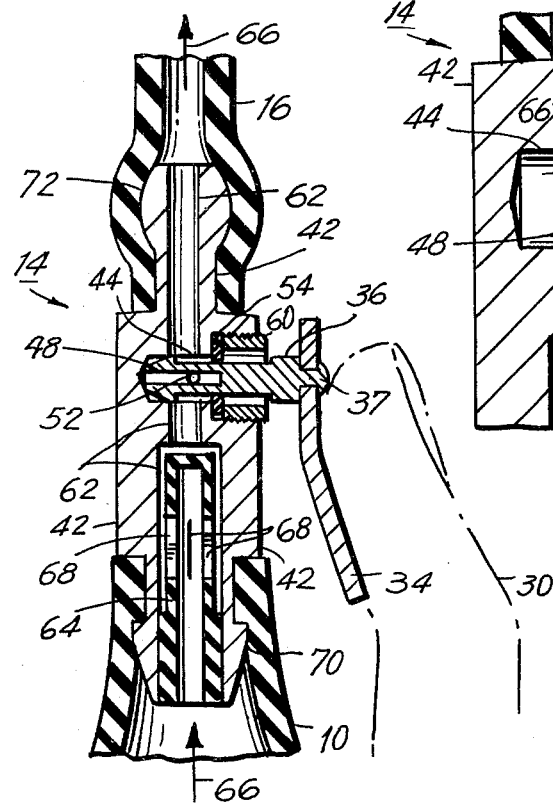
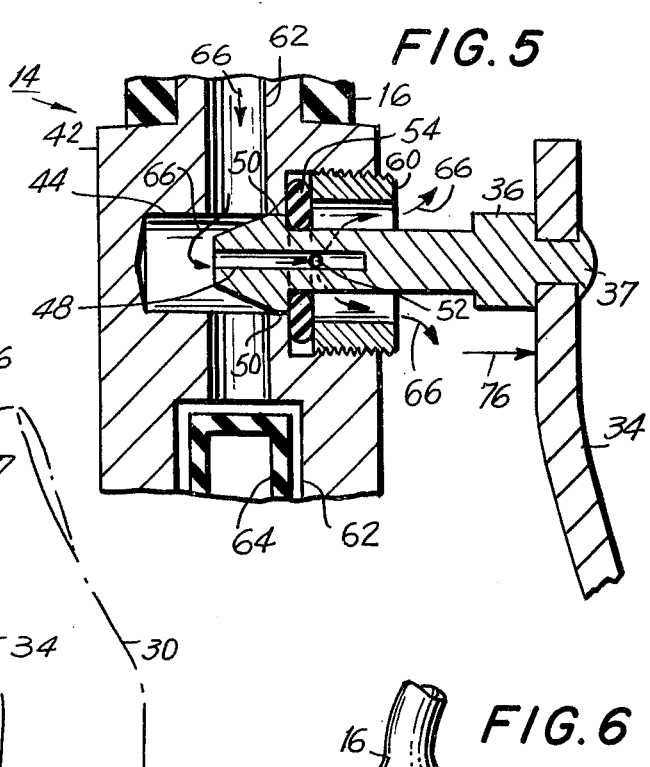
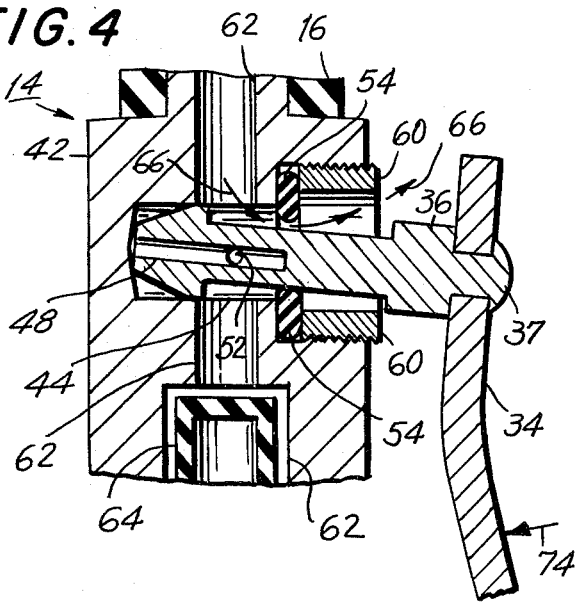
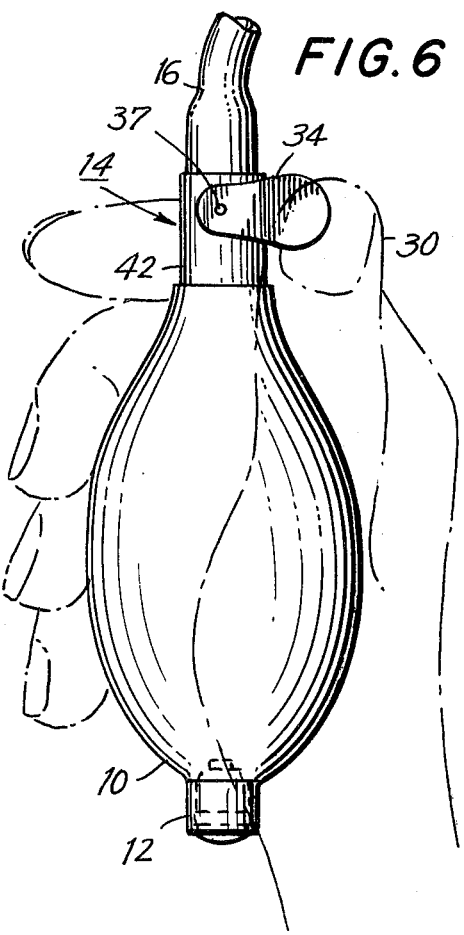

VALVE ASSEMBLY FOR A SPHYGMOMANOMETER

BACKGROUND OF THE INVENTION

1. Field of the Invention

Sphygmomanometer pressure relief valves.

2. Description of the Prior Art

A basic sphygmomanometer now in common use includes a resilient bulb which is manually repeatedly squeezed to pump air through a tube into an inflatable cuff which is wrapped around a person's arm. A pressure gauge is connected to the cuff to indicate the pressure level, and a manually operable valve is provided to slowly bleed air from the inflated cuff while a physician listens on a stethoscope to the pulsation of blood through an artery and concomitantly reads the gauge to determine diastolic and systolic blood pressures. After the blood pressure measurements, have been taken, the valve is operated to release the pressure in the cuff so that the cuff may be removed from the person's arm. Various structures for such sphygmomanometer bleed valves are described in U.S. Pat. Nos. 3,254,671; 2,934,061 and 2,603,210.

SUMMARY OF THE INVENTION

1. Purposes of the Invention

It is an object of the present invention to provide an improved sphygmomanometer bleed valve.

Another object is to provide such a valve which is more convenient to use than valves now available, constitutes relatively few and simple parts, and is inexpensive to manufacture, reliable, efficient and easy to maintain.

An additional object is to provide such a valve in which the valve actuator can be manipulated, and the valve controlled, with a single finger of the same hand that squeezes the resilient bulb that supplies pressurized air to the cuff.

A further object is to provide such a valve in which very accurate air bleed rates can be maintained or adjusted as desired.

Still another object is to provide such a valve which may be readily adjusted to provide rapid release of air pressure from and deflation of the cuff of the sphygmomanometer.

Still a further object is to provide such a valve for a sphygmomanometer which enables highly accurate blood pressure measurement to be obtained.

These and other objects and advantages of the present invention will become evident from the description which follows.

2. Brief Description of the Invention

In the present invention, a bleed valve for a sphygmomanometer is provided which has three alternative operative positions. A first position of the valve is that in which the bleed is closed while the cuff is being inflated with air by repeatedly squeezing the resilient bulb. The second position is that in which the bleed valve is "cracked" temporarily, i.e., slightly opened when air is being slowly bled from the cuff and blood pressure is being determined. The third position is that in which the bleed valve is opened and maintains itself open when the blood pressure measurements are completed and release of air pressure from the cuff is effected to deflate the cuff so that it may be easily removed from the arm or leg of the person whose blood pressure is being measured.

The bleed valve is attached to a body with an air passageway and a transverse bore extending to said valve. Conveniently, the valve is integrated with the body and is close to the bulb. Suitable coupling means are provided at the ends of the body for connection to the bulb and to a tube which leads to the cuff. A check valve is disposed in the air passageway adjacent the bulb coupling means to permit air under pressure to flow into the tube but not backwards into the bulb.

The bleed valve includes a valve stem which extends into the transverse bore which constitutes a chamber. The valve stem is formed with a central axial bore that runs from the inner end of the stem to a terminus within the stem. At least one transverse passageway is provided in the stem that extends from the central axial bore to the outer surface of the stem.

The outer end of the transverse bore terminates at a recess at the base of which a resilient O-ring is seated. The O-ring has a central opening with an inner diameter slightly smaller than the outer diameter of the valve stem. The valve stem passes through this opening and forms a seal therewith when the valve is idle. If the valve stem is tilted, as about its inner end, the stem will stretch O-ring to create a gap between the stem ring through which pressurized air will leak, i.e., bleed. The O-ring is maintained in position by a nipple screwed into the recess and bearing against the ring. The bore of the nipple exceeds the diameter of the valve stem to leave enough clearance for the stem to be tilted. Removal of the valve stem from the body is prevented by an enlargement at the inner end of the valve stem. The enlargement is spaced from the O-ring in idle position of the bleed valve to permit outward displacement of the stem to an extent sufficient to shift the transverse opening in the stem outwardly of the ring and thus form a connection from the air passageway to the ambient surroundings through which air can escape.

Means such as a curved lever is attached to the outer end of the valve stem in such a location, near the bulb, as to facilitate tilting of the valve by the thumb of the hand used to inflate the cuff. When the valve stem is shifted inwardly the valve is placed in its first setting. If, then, the inwardly displaced valve stem is tilted by the lever air is slowly bled from the cuff as long as the stem is tilted, this being the second setting. When the valve stem is shifted outwardly, the valve is placed in its third setting and will remain there after the manipulative force is removed, due to the frictional restraint of the O-ring on the stem.

The invention accordingly consists in the features of construction, combination of elemens, and arrangement of parts which will be exemplified in the device hereinafter described and of which the scope of application will be indicated in the appended claims.

BRIEF DESCRIPTION OF THE DRAWINGS

In the accompanying drawings in which is shown one of the various possible embodiments of the invention:

FIG. 3 is an enlarged sectional view taken substantially along the line 3—3 of FIG. 1;

FIG. 4 is an enlarged axial sectional view of the valve in its second air bleed position;

FIG. 5 is an enlarged sectional view of the valve in its third, i.e. relief, position; and FIG. 6 shows an alternative positioning of the curved lever.

DETAILED DESCRIPTION OF THE PREFERRED EMBODIMENTS

Figures 1, 2:
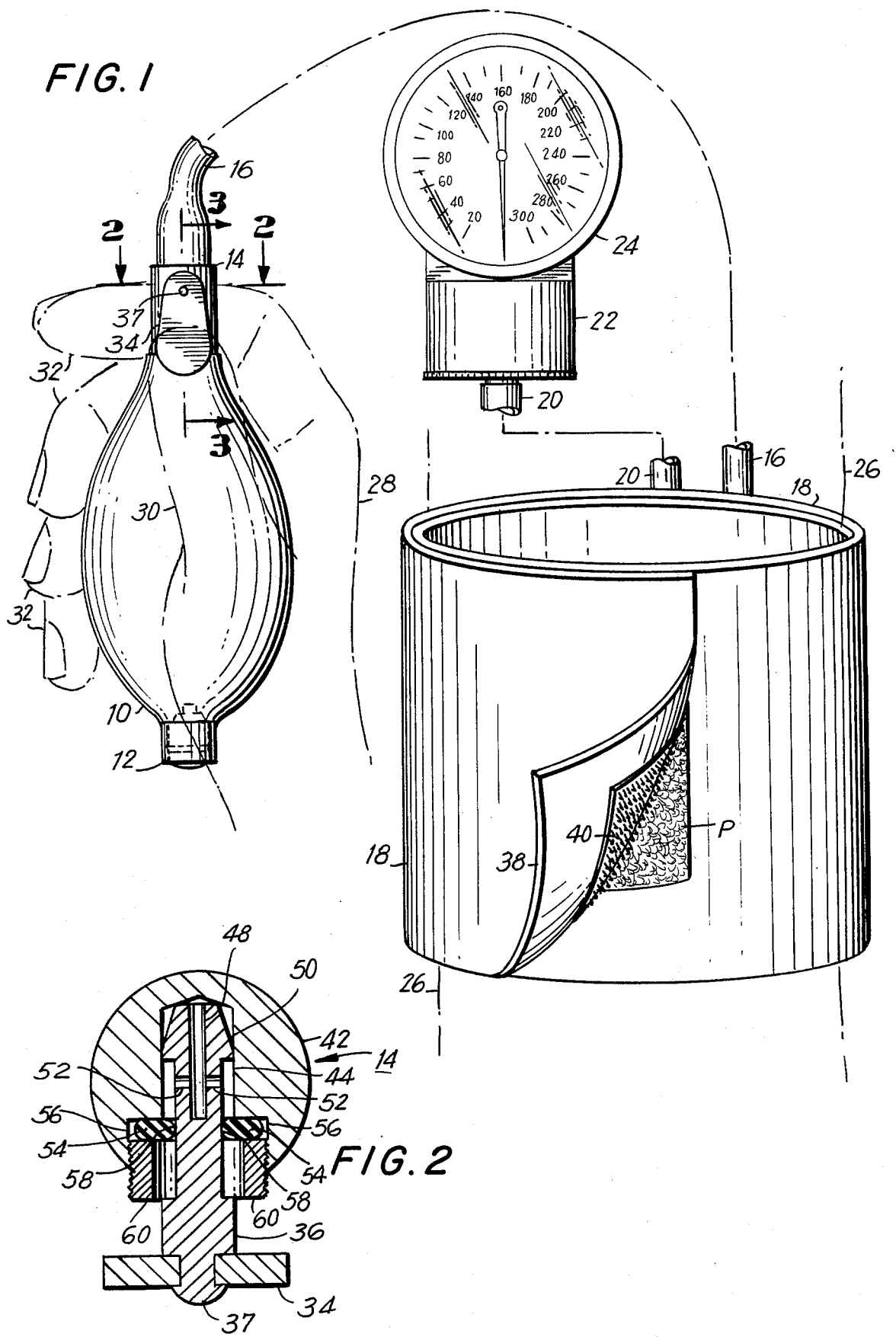
FIG. 1 is a fragmentary view of the sphygmomanometer with the new bleed valve.
FIG. 2 is an enlarged sectional view taken substantially along the line 2—2 of FIG. 1.

Referring now to FIG. 1, the sphygmomanometer includes a flexible resilient pumping bulb 10 having a lower intake check valve 12, a bleed valve 14 of the present invention located between the bulb 10 and a pressure tube 16 which extends to a cuff 18, and a gauge tube 20 which extends from the cuff 18 to a pressure measuring device 22 i.e., a gauge 24.

The bulb 10 is generally composed of natural or artificial rubber or an elastomeric plastic such as polyvinyl chloride, polyethylene, polypropylene, etc. The bulb 10 is provided with the intake check valve 12 which is of conventional configuration and permits the ingress of air into the bulb 10 but prevents egress of air therethrough. In FIG. 1 the cuff 18 is arranged to define an annulus in which form it is mounted on a patient's arm or leg shown as 26 in phantom. The cuff 18 is designed to be inflated with air with consequent pressurization preparatory to the measurement of blood pressure via readings on the gauge 24, as is commonly understood by those skilled in the art. A hand 28 of a physician or nurse is shown in phantom grasping the bulb 10, between the heel of the hand and the opposing fingers 32 in which position the bulb is pumped (alternatively squeezed and released) so that air is periodically drawn into the bulb 10 and then forced through the valve 14 and the hose 16 into the cuff 18.

A lever 34 is the control element of the valve 14. The lever 34 is mounted on the valve with one end attached to the projecting outer terminus of a valve stem 36. The user's thumb 30 is shown in valve controlling position on the lever in FIG. 1, no pressure being applied by the thumb to the lever 34. The lever is freely rotatable about a pin 37 coaxial with and projecting from the stem so that the valve stem is perpendicular to longitudinal axis of the lever. In FIGS. 1, 2 and 3 the valve stem is positioned fully inwardly within the valve 14 in fully closed (first) position of said valve.

The cuff 18 is of standard construction and constitutes an outer hollow air-impermeable cloth tube 38 and an inner padded Velcro lining 40 adapted to engage a Velcro patch P on the outer face of the tube for firm positioning of the cuff on the arm 26.

FIG. 2 shows internal details of the bleed valve 14. The valve includes an elongated (see FIG. 3) body member 42. The valve stem 36 has its inner end located in a chamber 44 within the body member 42. The valve stem 36 extends into the chamber from an outer end on which the lever 34 is mounted. The valve stem 36 has a central axial bore 48 extending outwardly from the inner end of the stem in the chamber 44. An enlargement with a shoulder 50 is provided on the inner end of the stem. Lateral branches 52 run from the central axial bore to the outside of the stem.

Air flow out of the chamber 44 to the outside atmosphere is prevented by a resilient O-ring 54 which is seated in a circular recess 56 coaxial with the cavity 44. The inner surface 58 of the O-ring is slightly smaller than the outer diameter of the stem 36 and forms a sliding sealing fit therewith. The O-ring is sealingly retained in the recess 56 by a threaded sleeve 60 which is screwed into female threads in the recess 56. The outer end of the sleeve 60 may be notched (not shown) to facilitate turning of the sleeve 60 by a spanner. The sleeve and the base of the recess conjointly define an annular groove in which the O-ring is captive. The groove is somewhat deeper than the ring to allow a small outward shifting of a portion of the ring for a purpose described hereinafter. The ring is lightly squeezed by the sleeve to ensure a sealing fit on the valve stem and to seal the mouth of the chamber 44.

Referring now to FIG. 3, further internal details of the valve 14 are shown, including an axial air passageway 62 which runs completely through the body 42, as well as an egress check valve 64 which permits movement of pressurized air 66 from the bulb 10 upon squeezing the bulb, but prevents return movement of pressurized air back into the bulb from the tube 16 when the manual pressure on the bulb is released. The check valve 64 is a flexible resilient tubular member with an open lower end mounted in the ingress end of the air passageway 62 and a closed upper end. A plurality of longitudinal slits 68 are provided in the side walls of the member 64. The upper portion of the member 64 is spaced from the side walls of air passageway 62. When the bulb 10 is squeezed, air therein is forced into the member 64 under pressure; the upper part of member 64 expands laterally, opening the slits 68 to permit outward passage of air into the egress end of the axial bore 62 through the cavity 44 and into the tube 16. When the pressure on bulb 10 is released and the bulb expands to its normal fully rounded configuration, air at atmospheric enters the bulb through the ingress check valve 12 so that the slits 68 close.

The lower end of the elongated body 42 is secured in the upper end of the bulb 10 by a fitting 70 at the lower end of the body. A similar fitting 72 is provided at the upper end of the body for attachment of the tube 16.

Assuming that the cuff has been inflated, FIGS. 2 and 3 show the valve stem in blocking (first) position in which no bleeding of air occurs. The lateral branches are within the cavity 44 so as to prevent loss of pressurized air through the central axial bore; the O-ring sealing engages the valve stem so that no pressurized air is lost by flow along the stem.

FIG. 4 shows how air may be slowly and controllably bled from the cuff 18 so that accurate blood pressure readings may be taken from the gauge 24. Manual application of a force 74 from a user's thumb on the lever 34 which conveniently may be parallel to the longitudinal axis of the body 42 and extending toward the bulb causes the valve stem to pivot about the inner end of the stem, more specifically the enlargement, which for easy pivoting has a diameter just slightly smaller than that of the cavity 44, thereby somewhat enlarging the O-ring 54 and leaving a small arcuate opening between a part of the O-ring 54 and the valve stem 36 through which a pressurized air stream 66 can escape from the cavity to the atmosphere. The enlargement of the O-ring is eased by the excess depth of the groove in which the O-ring is located. This enlargement is temporary and momentary. It persists only as long as the valve stem is tilted. Such operation is particularly simple because the lever provides a mechanical advantage and is located near the bulb for ready operation by the thumb of the hand of the user employed to squeeze the bulb.

FIG. 5 shows the position of the valve stem for full release of pressurized air from the cuff 18 without continuous application of force to the stem, this position being the one used after the blood pressure measurements have been completed. A manual force 76 is applied to the lever 34 adjacent to the stem 36 and in an outward direction coaxial with the stem and away from the bleed valve to linearly displace the stem away from the body 42 and partially out of the cavity 44. Removal of the stem is prevented by contact of the shoulder 50 with the O-ring 54. In the outwardly displaced (third) position of the valve stem 36 an air stream 66 flows through the axial bore 62 and out of the transverse branches which at this time have been shifted outwardly beyond the O-ring so that they have access to the atmosphere.

Subsequent application of a manual force opposite to the force 76 will return the valve stem 36 to the closed (first) position of FIGS. 2 and 3 for future use. Similar considerations apply to the FIG. 4 disposition of the valve stem 36, i.e. removal of the manual force 74 in FIG. 4 stops the bleed flow of the air stream 66 and returns the valve stem 36 to the position of FIGS. 2 and 3 since the O-ring 54 is composed of resilient material.

FIG. 6 illustrates how the lever 34 may be rotated about the axis of the valve stem 36, so that the lever 34 may also be operated by the thumb 30 in other positions.

It will be appreciated that a feature of the present invention is the provision of a manually manipulatable biased control element carried by a body associated with the bleed valve which element is so located as to be readily accessible to the tip of a finger of the hand used to pump the bulb, said control element being pivotally mounted on the body whereby it easily can be depressed against the bias that normally closes the valve so that finger pressure on the pivoted element can accurately regulate the rate at which air is bled from the cuff.

It thus will be seen that there is provided a bleed valve for a sphygmomanometer which achieves the various objects of the invention and which is well adapted to meet the conditions of practical use.

As various possible embodiments might be made of the above invention, and as various changes might be made in the embodiment above set forth, it is to be understood that all matter herein described or shown in the accompanying drawings is to be interpreted as illustrative and not in a limiting sense.

Having thus described the invention, there is claimed as new and desired to be secured by Letters Patent:

1. A valve assembly for a sphygmomanometer comprising a body having an air passageway, a pumping bulb, coupling means at one end of said passageway to connect said body to the pumping bulb, a sphygmomanometer cuff, coupling means at the other end of said passageway to connect said body to said sphygmomanometer cuff, an egress check valve adjacent said bulb, an ingress check valve at an ingress opening to said bulb, a bleed valve adjacent said bulb and connected to said air passageway, said egress check valve being located between said bleed valve and an egress opening from said bulb, said bleed valve having an operating member accessible to a finger of a user's hand employed to pump the bulb, said bleed valve including a valve stem, said valve stem having a free floating pivoting mounting so that said valve stem is manually movable to three positions including a first position in which the valve is closed and will remain closed unless manually displaced therefrom, a second position in which the valve is open and will remain open unless manually displaced therefrom, and a third position to which the valve stem manually is pivotally tilted and the valve is open, said valve stem being axially manually shiftable between its first and second positions, and resilient means to bias the valve stem from its third position to its first or second position or to any axial position intermediate said first and second positions.

2. A valve assembly as set forth in claim 1 wherein the bleed valve includes an open-mouthed cavity in communication with the air passageway, a resilient O-ring, means to support said O-ring in sealing position over the mouth of said cavity, said valve stem including a portion extending through the opening in the O-ring in slidable sealing engagement therewith, said valve stem being tiltable about a fulcrum constituting a portion of the stem within the cavity thereby to stretch the O-ring and open a passageway between a portion of the stem and an associated portion of the opening of the O-ring through which air under pressure can flow out of the air passageway to the surrounding atmosphere.

3. A valve assembly as set forth in claim 2 wherein the valve stem has a passageway extending from its end within the cavity to at least one laterally extending branch terminating at a side wall of the stem, said termination of said branch being located within the cavity in the first position, and beyond the O-ring and exposed to the surrounding atmosphere in the second position.

4. A valve assembly as set forth in claim 3 wherein the stem has an enlargement adjacent the end thereof within the cavity to prevent withdrawal of the stem from the cavity.

5. A valve assembly as set forth in claim 1 wherein the operating member constitutes a lever and means mounting the lever on the outer end of the stem at right angles to the longitudinal axis of the stem.

6. A valve assembly as set forth in claim 5 wherein the mounting means permits rotation of the lever around the longitudinal axis of the stem.

7. A valve assembly as set forth in claim 6 wherein the lever is curved to present an outwardly concave surface.

8. A valve assembly for a sphygmomanometer comprising a body having an air passageway, a pumping bulb, coupling means at one end of said passageway to connect said body to the pumping bulb, a sphygmomanometer cuff, coupling means at the other end of said passageway to connect said body to said sphygmomanometer cuff, an egress check valve adjacent said bulb, an ingress check valve at an ingress opening to said bulb, a bleed valve adjacent said bulb and connected to said air passageway, said egress check valve being located between said bleed valve and an egress opening from said bulb, said bleed valve having a manually manipulatable control element positioned to be readily accessible to the finger tip of the hand of a user pumping the bulb, said control element being freely floating and pivotally mounted for movement from a valve closed position to a valve bleeding position, and resilient means to bias the control element to valve closed position, whereby said control element can be depressed against the bias so that finger pressure on said pivoted control element can accurately regulate the rate at which air is bled through said air passageway from said sphygmomanometer cuff.

* * * * *